United States Patent
Bakry (10) Patent No.: US 6,846,292 B2
(45) Date of Patent: Jan. 25, 2005

(54) PLEURAL BIOPSY AND BRUSHING NEEDLE

(76) Inventor: Mohamed Bakry, 501 6$^{th}$ St., 9A, Brooklyn, NY (US) 11215

(*) Notice: Subject to any disclaimer, the term of this patent is extended or adjusted under 35 U.S.C. 154(b) by 198 days.

(21) Appl. No.: 10/078,903

(22) Filed: Feb. 19, 2002

(65) Prior Publication Data

US 2003/0158498 A1 Aug. 21, 2003

(51) Int. Cl.$^7$ ............................................. A61B 10/00
(52) U.S. Cl. ...................... 600/564; 600/569; 600/570; 606/170; 604/22
(58) Field of Search ........................... 604/22; 606/172, 606/174, 170, 167, 180–183; 600/562–572

(56) References Cited

U.S. PATENT DOCUMENTS

| | | | |
|---|---|---|---|
| 2,541,246 A | * 2/1951 | Held | ........................... 606/205 |
| 3,960,153 A | 6/1976 | Carey et al. | |
| 4,105,031 A | 8/1978 | Kurtz et al. | |
| D250,207 S | 11/1978 | Kurtz et al. | |
| 4,153,058 A | 5/1979 | Nehme | |
| D255,937 S | 7/1980 | Kurtz et al. | |
| 4,439,189 A | 3/1984 | Sargeant et al. | |
| 4,729,374 A | * 3/1988 | Alfranca | ..................... 606/171 |
| 5,301,684 A | * 4/1994 | Ogirala | ....................... 600/567 |
| 5,306,284 A | * 4/1994 | Agee et al. | .................. 606/170 |
| 5,320,110 A | 6/1994 | Wang | |
| 5,344,410 A | 9/1994 | Kolkin et al. | |
| 5,431,633 A | 7/1995 | Fury | |
| 5,484,401 A | 1/1996 | Rodriguez et al. | |
| 5,489,264 A | 2/1996 | Salo | |
| 5,649,547 A | * 7/1997 | Ritchart et al. | ............. 600/566 |
| 5,797,906 A | * 8/1998 | Rhum et al. | ................... 606/48 |
| 6,059,734 A | * 5/2000 | Yoon | ........................... 600/565 |
| 6,077,290 A | * 6/2000 | Marini | ........................ 600/564 |
| 6,254,581 B1 | 7/2001 | Scott | |
| 6,363,940 B1 | * 4/2002 | Krag | .......................... 606/184 |
| 6,447,525 B2 | * 9/2002 | Follmer et al. | ............. 606/159 |

* cited by examiner

Primary Examiner—Charles Marmor
(74) Attorney, Agent, or Firm—Roger M. Rathbun

(57) ABSTRACT

A biopsy needle and method of using the same. The biopsy needle includes a pair of articulating members that can be moved between a retracted position where the articulating members are contained within the biopsy needle and an extended position where the articulating members extend outwardly from the distal end of the biopsy needle into the pleural cavity of a patient. Once extended, the articulating members have operative surfaces that contact the parietal pleura of the patient such that a biopsy sample can be obtained as the operative surfaces are moved in contact with the parietal pleura. The operative surfaces may be a brush blade or a knife blade. A passageway within the interior of the biopsy needle allows removal of fluids from the patient.

23 Claims, 4 Drawing Sheets

PLEURAL BIOPSY AND BRUSHING NEEDLE

BACKGROUND

The present invention relates to biopsy needles, and, more particularly, to an improved biopsy and brushing needle that can be used to obtain tissue samples of the parietal pleura for biopsy examination purposes and to more easily permit thoracentesis procedures. The present invention also provides a needle and method of using the same to facilitate a technique of brushing the parietal pleura for more effective tissue sampling.

In the course of carrying out an in depth examination of certain at risk patients, there is a need to obtain a biopsy of the parietal pleura, that is, the layer inside the rib cage and within the pleural cavity. Due to the closeness of the pleural cavity to the lung, it is often advantageous to take the biopsy from that parietal pleura in order to assess the condition of the lung since a biopsy of the lung itself is quite difficult and there is a real danger of puncturing the lung during the procedure. As such, resort is made to the use of a biopsy of the parietal pleura to remove a sample of that tissue and which is generally indicative of the condition of the lung and less dangerous to the patient.

In order to obtain a biopsy of the patient's parietal pleura, however, there are basically two devices that are currently available and widely used and each has certain drawbacks. Each of the current devices is shown and described in U.S. Pat. No. 5,320,110 of Wang as prior art to that patent. As described in the Wang patent, there is a Cope needle shown in FIGS. 1–3 and the further description illustrates a fairly complex and rigorous series of steps that must be carried out in order to obtain a sample of the tissue of the parietal pleura.

One of the features of the Cope needle is the presence of a hook located at the distal end of the Cope needle and which hooks the tissue from the parietal pleura to withdraw that sample. However, one of the drawbacks in the use of the Cope needle is that the use of a distally located hook in the needle is inserted through the rib cage to enter the pleural cavity, however it is sometimes difficult to determine precisely where the distal end is located when the needle is activated to obtain the biopsy sample. Thus the biopsy sample may be taken from the desired parietal pleura or may be taken from some other location within the anatomy of the patient.

The other biopsy needle, again referred to and described in the aforementioned Cope needle, is the Abrams needle and, again, the needle is inserted into the pleural cavity where the sample of the tissue is desired to be removed therefrom. With the Abrams needle there is a cutting mechanism that is actually located at the distal end of the needle and which is manipulated by the user to cut a portion of the tissue for subsequent removal and analysis. Again, however, with the Abrams needle, while effective, there is no positive indication when the distal end of the needle is properly positioned with the pleural cavity so as to remove the tissue from the desired parietal pleura and thus, it is possible, with that needle, to obtain a sample from some area of the anatomy other than the proper location within the pleural cavity.

Accordingly, it would be advantageous to provide a biopsy needle for obtaining a biopsy sample of tissue from the parietal pleura in a more predictable manner and to be sure that the sample is removed from the correct location within the patient and, further, where the procedure for obtaining that biopsy sample is relatively easy to carry out with accuracy.

SUMMARY OF THE INVENTION

Accordingly, the present invention relates to an improved biopsy needle that can be utilized effectively and accurately to remove a biopsy sample of tissue from the parietal pleura of a patient. In the present invention, there is a positive indication to the user when the distal end of the needle is properly positioned so as to obtain a biopsy sample from the proper and desired area within the proper location from the pleural cavity of a patient, that is, from the parietal pleura of a patient.

In the biopsy needle of the present invention, the needle comprises an outer tube having a distal end that is preferably pointed so as to easily penetrate through the rib cage of a patient and be positioned within the pleural cavity of a patient. As such, in the use of the present biopsy needle, the outer tube can be inserted by the user through the rib cage so as to properly penetrate into the pleural cavity where the biopsy tissue sample is desired to be removed.

The proximal end of the biopsy needle of the present invention remains located outside of the patient when the distal end is properly positioned by the user. The outer tube itself is hollow and has at least one opening located at or proximate to the distal end of the outer tube. In the preferred embodiment, there are two openings in the outer tube and those two openings are preferably located about the periphery of the outer tube spaced about 180 degrees apart. An inner tube is interfitted within the outer tube and is axially movable therein. The inner tube has a distal end that is located at about the distal end of the outer tube and has a proximal end that is accessible to a user external of a patient. Preferably, the proximal end of the inner tube extends outwardly from the proximal end of the outer tube. In the preferred embodiment, the proximal end of the inner tube is formed as an enlarged diameter portion that serves as a handle to be manipulated by the user to move the inner tube axially within the outer tube.

At the distal end of the inner tube, there is located at least one articulating member, and, again, preferably there are two of such articulating members. Whether one or two, the articulating member or members are aligned with respect to the opening or openings proximate the distal end of the outer tube. The articulating members are pivotally affixed to the distal end of the inner tube and can pivot from a position generally in alignment with or at an acute angle with respect to the longitudinal axis of the inner tube to a position about 90 degrees to that longitudinal axis.

In the biopsy needle of the present invention, the user can manipulate the proximal end of the inner tube to cause the articulating member or members to move between a retracted position where the outer profile of the outer tube is unaffected by the articulating member and an extended position where the articulating member or members project outwardly from the distal end of the outer tube by passing through the opening or openings in the outer tube.

The articulating members can therefore be moved to an extended position projecting outwardly from the distal end of the outer tube and the articulating members may have a knife edge, a brush edge or any combination of the two edges. For example, if there are two articulating members, one may have a knife edge and the other a brush edge. Alternatively, of course, both articulating members may have brush edges or knife edges, or there may only be one articulating member used in the present invention and which may have either a knife edge or a brush edge that is, when the articulating members are in the extended positions, that operative edge faces outwardly towards the exterior of the patient such that the knife or brush edge of the articulating member can face the parietal pleura of the patient.

Accordingly, the use of the present invention can now be described and will be explained with respect to the preferred embodiment wherein there are two articulating members utilized. The biopsy needle is inserted through the rib cage of a patient, assisted by the pointed profile of the outer tube, so that the distal end is located within the pleural cavity of a patient. Once so located, the proximal end of the inner tube can be manipulated by the user, preferably by contacting the handle and moving the inner tube axially with respect to the outer tube whereupon the articulating members are caused to move from their retracted position not affecting the outer profile of the outer tube, to an extended position wherein the articulating members are both extending outwardly from the distal end of the outer tube and into the pleural cavity of a patient. In order to extend the articulating members to the extended position, it is paramount that the distal end of the biopsy needle be located with that pleural cavity so that the user is assured that the needle is properly positioned.

The proper position of the distal end of the present biopsy needle, however, is assured by the very operation and use of the needle itself. In order to properly extend the articulating member or members, the distal end of the biopsy needle needs to be in the proper position within the patient, that is, the user is assured that the distal end of the biopsy needle is properly positioned within the pleural cavity by the ability to extend the articulating member or members.

Once properly positioned, and the articulating members extended, the user can then move the biopsy needle slightly outwardly within the pleural cavity so that the operative edges of the articulating members can physically contact the parietal pleura of a patient. Thereupon, by simply rotating the biopsy needle, the knife edge or the brush edge can move in contact with the parietal pleura and collect the desired sample of tissue. If the articulating member has a knife edge, the articulating member will cut a sample of the tissue, wherein, if the articulating member has a brush edge, the brush edge will pick up cells and tissue on the surface of the parietal pleura. If both a knife edge and a brush edge are utilized, of course, both functions will be carried out simultaneously. At the end of the sample gathering, the proximal end of the inner tube is again manipulated by the user to return the articulating members back to their retracted position so that the biopsy needle can easily be withdrawn from the patient and the sample obtained.

As a further feature, there may be an access opening located at or near the proximal end of the outer tube that communicates through the interior of that outer tube with the openings in the distal end of the outer tube so that the user can withdraw a sample of fluid from within the pleural cavity as desired to carry out the procedure of thoracentesis. There may be a flexible tube that communicates with the access opening having a free end with a connector, such as a stopcock, so that a syringe or other fluid withdrawing device can be connected thereto to withdraw those samples of fluid from the pleural cavity of the patient.

Additional features and advantages of the invention will become apparent to those skilled in the art upon consideration of the following detailed description of preferred embodiments exemplifying the best mode of carrying out the invention.

DETAILED DESCRIPTION OF THE INVENTION

Figure 1:
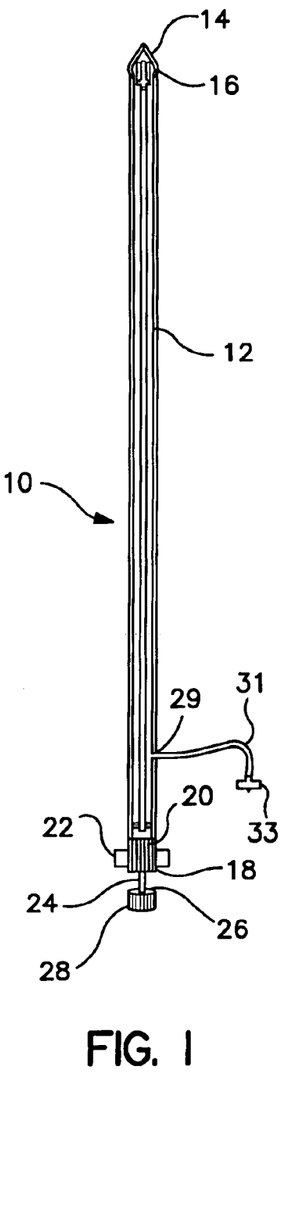
FIG. 1 is a side cross-sectional view of a biopsy needle constructed in accordance with the present invention showing the operative components in the retracted position.

Referring now to FIG. 1, there is shown a side cross sectional view of a biopsy needle 10 constructed in accordance with the present invention. As can be seen in the Figure, the biopsy needle 10 comprises an outer tube 12 having a distal end 14 that is shaped in a pointed profile to enable the biopsy needle 10 to penetrate the rib cage of a patient in the utilization of the biopsy needle 10. At or proximate to the distal end 14, there are formed a pair of openings 16, preferable spaced apart about the periphery of the outer tube 12 at about 180 degrees separation and the purpose of the openings 16 will be later explained. The biopsy needle 10 also has a proximal end 18 that remains outside of a patient during the use of the present biopsy needle 10 and there preferably is an outer tube cover 20 that seals off the proximal end of the outer tube 12. A pair of cover holder wings 22 extend outwardly from the outer tube cover 20 to enable the user to adequately engage the proximal end of the biopsy needle 10.

An inner tube 24 is located within the hollow interior of the outer tube 12 and has a proximal end 26 that extends outwardly from the proximal end 18 of the outer tube 12. The inner tube 24 passes through the outer tube cover 20 and can be moved axially along its longitudinal axis within the outer tube 12 while retaining a seal as it passes through the outer tube cover 20. A handle 28 is formed at the proximal end 26 of the inner tube 24 that is an enlarged diameter so as to be readily gripped by a user in carrying out the intent of the present invention. The inner tube 24 extends along the internal hollow area of the outer tube 12 to a distal end 30 that is positioned at or about the distal end 14 of the outer tube 12. There also can be seen a pair of articulating members 32 that are pivotally affixed to the distal end 30 of the inner tube 24. As will be seen, the articulating members 32 can be moved between a retracted position, as shown in FIG. 1, where they are fully contained within the interior of the outer tube 12 and an extended position where the articulating members 32 extend outwardly from the outer tube 12 through the openings 16. In the retracted position of FIG. 1, the outer profile of the outer tube 12 is not affected by the position of the articulating members 32 and therefore the biopsy needle 10 can be used to pierce the rib cage of a patient with a clean profile without the articulating members 32 having any deleterious effect on the piercing of the patient's rib cage or in any way obstructing that procedure.

As further can be seen in FIG. 1, there is an access opening 29 located at or in close proximity to the proximal end of the outer tube 12 an which provides communication with the interior of the outer tube 12. A flexible tube 31 is provided to communicate with the access opening 29 and a connector 33, such as a stopcock, is located at the free end of the flexible tube 31 so that a user can connect a withdrawing device, such as a syringe, not shown, to create a partial vacuum within the interior of the outer tube 12 to withdraw fluids from a patient through the outer tube 12 to effect the procedure of thoracentesis.

Figure 2:
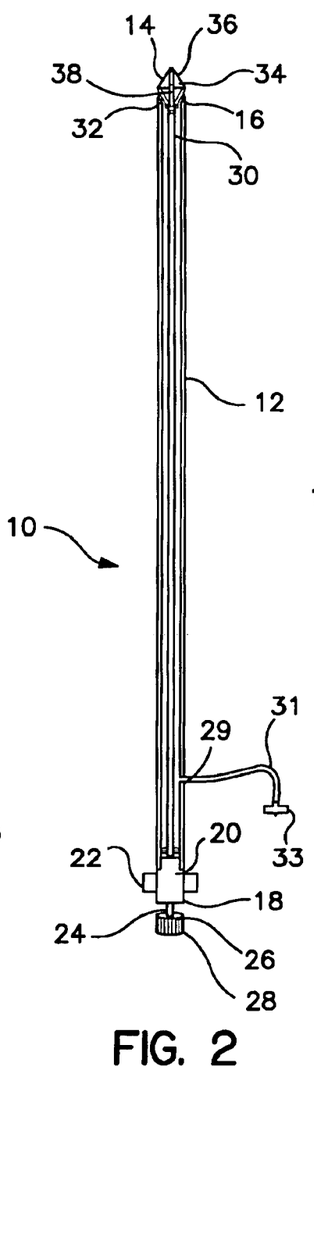
FIG. 2 is a side cross sectional view of the biopsy needle of FIG. 1 in an intermediate position.

Turning now to FIG. 2, there is shown a side view, partly in cross section, of the biopsy needle 10 with the articulating members 32 in an intermediate position and better showing the inner tube 24 that extends along the interior of the outer tube 12. In FIG. 2, the articulating members 32 are in an intermediate position, that is, the articulating members 32 have been moved from the fully retracted position of FIG. 1 but still do not do not affect the outer profile of the outer tube 12.

There can also be seen in FIG. 2, that the free ends of the articulating members 32 contact a flat surface 34 formed in the internal area of the distal end 14 of the outer tube 12. An elongated groove 36 is also formed in the internal area of the distal end 14 of the outer tube 12 and which receives an extended needle shaped tip 38 formed in or as the distal end 30 of the inner tube 24. Since, as stated, the inner tube 24 is axially movable along its longitudinal axis within the outer tube 12, there is a stability provide by the needle shaped tip 38 that rides within the elongated groove 36.

Figure 3:
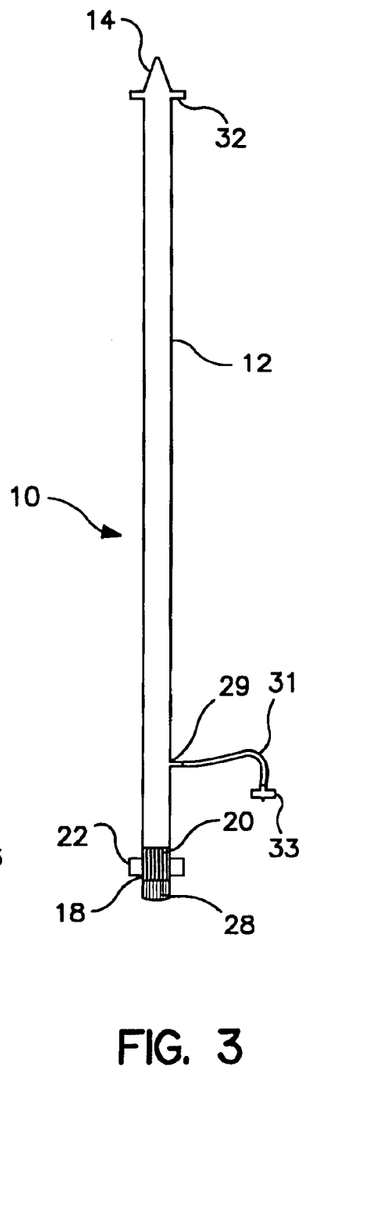
FIG. 3 is a side view of a biopsy needle of FIG. 1 with the operative components in the extended position.

Turning now to FIG. 3, taken along with FIG. 2, there is shown a side view of the present biopsy needle 10 in which the articulating members 32 have been moved to their extended positions. Thus, as can be seen, the handle 28 has been moved inwardly to axially move the inner tube 24 toward the distal end 14 of the outer tube 12, thereby pushing the articulating members 32 against the flat surface 34 where the articulating members 32 are forced outwardly though the openings 16 to the extended position shown in FIG. 3 where the articulating members 32 preferably project outwardly from the outer tube 12 at an angle of about 90 degrees to the longitudinal axis of the outer tube 12. As will be later explained, when the articulating members 32 are in their extended position of FIG. 3, the user can utilize the biopsy needle 10 to extract tissue samples from the parietal pleura of a patient.

Figure 4:
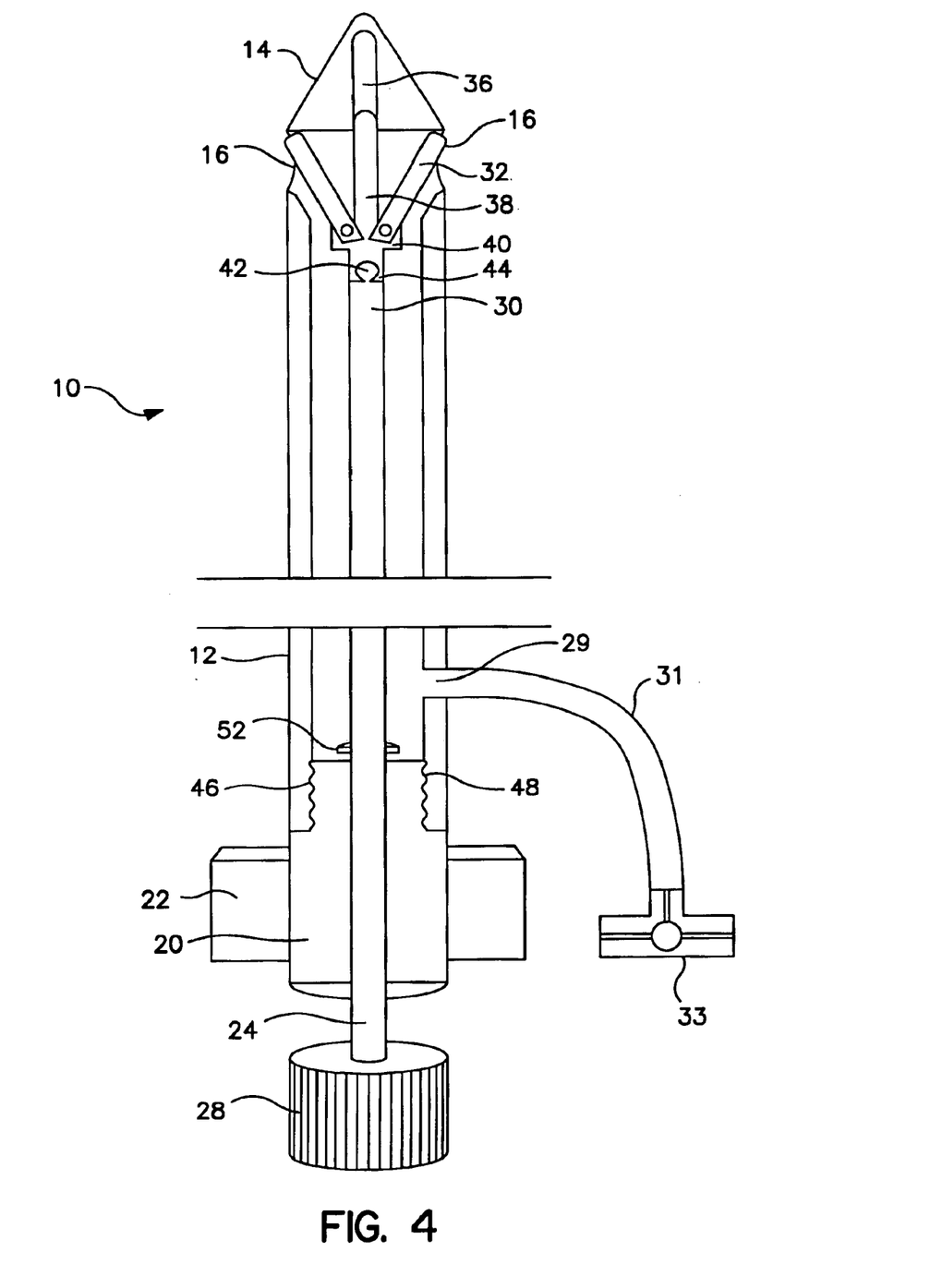
FIG. 4 is an enlarged cross sectional view of the biopsy needle of the present invention.

Turning now to FIG. 4, there is shown a cross section view of the biopsy needle 10 constructed in accordance with the present invention. While the articulating members 32 may be directly affixed to the distal end 30 of the inner tube 24, in the embodiment of this Figure, there is an additional component, that is, there is a T-shaped end tube 40 affixed to the distal end 30 of the inner tube 24 and is affixed thereto by some easily engagable snap-in arrangement such as the ball 42 formed at the distal end 30 of the inner tube 24 that interfits by snapping into a corresponding socket 44 formed in the base of the T-shaped end tube 40. Obviously, while the ball and socket arrangement is quite suitable for the interconnection of the inner tube 24 and the T-shaped end tube 40, other similar interconnecting means can be used.

With the embodiment of FIG. 4, therefore, the T-shaped end tube 40 has a needle shaped tip 38 formed therein and which slidingly fits into and rides within the elongated groove 36 formed in the inner area of the distal end 14 of the outer tube 12. As a further feature, the outer tube cover 20 has external threads 46 formed thereon and which are threadedly engaged with the internal threads 48 formed on the interior of the outer tube 12 so that the outer tube cover 20 can thereby be attached to and removed from the proximal end of the outer tube 12 by the threaded engagement therebetween. The innermost surface 50 of the outer tube cover 20 cooperates with a fixed stop 52 affixed to the inner tube 24 such that the fixed stop 52, which may be a C-clip or other device affixed to the inner tube 24 abuts against the innermost surface 50 when the inner tube 24 is attempted to be withdrawn from the outer tube 12 such that such withdrawal of the inner tube 24 is limited to a certain predetermined distance and the inner tube 24 is thereby prevented from being withdrawn too great a distance from the interior of the outer tube 12.

Figure 5:
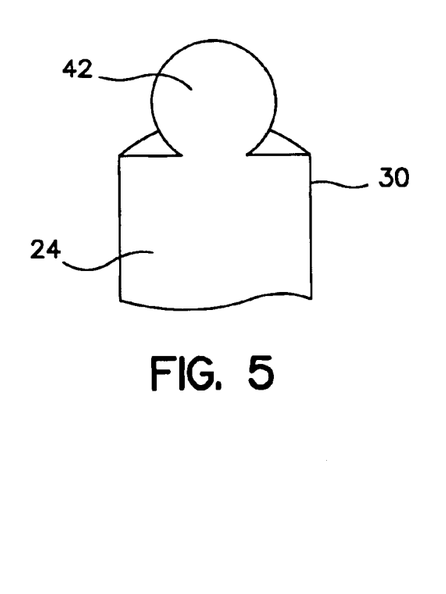
FIG. 5 is an enlarged sectional perspective view of the distal end of an inner tube according to one embodiment of the present invention.
Figure 6:
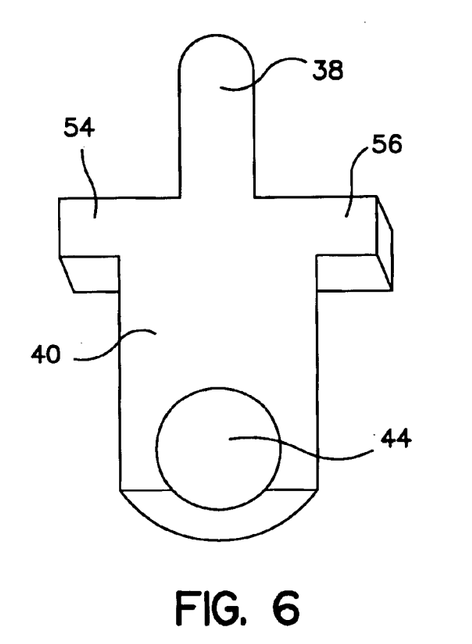
FIG. 6 is an enlarged sectional perspective view of a component of the present invention.

Turning now to FIG. 5, there is shown a sectional perspective view of the distal end 30 of the inner tube 24 and showing the ball 42 molded thereto and, in FIG. 6, there is shown a sectional perspective view of the T-shaped end tube 40 that is used with the FIG. 4 embodiment. As can be seen in FIG. 6, the socket 44 is formed in the base of the T-shaped end tube 40 with both legs 54, 56 of the T configuration extending outwardly therefrom. In addition, there is shown the needle shaped tip 38 that fits within the elongated groove (See FIG. 4) to guide the axial movement of the inner tube 24.

Figure 7:
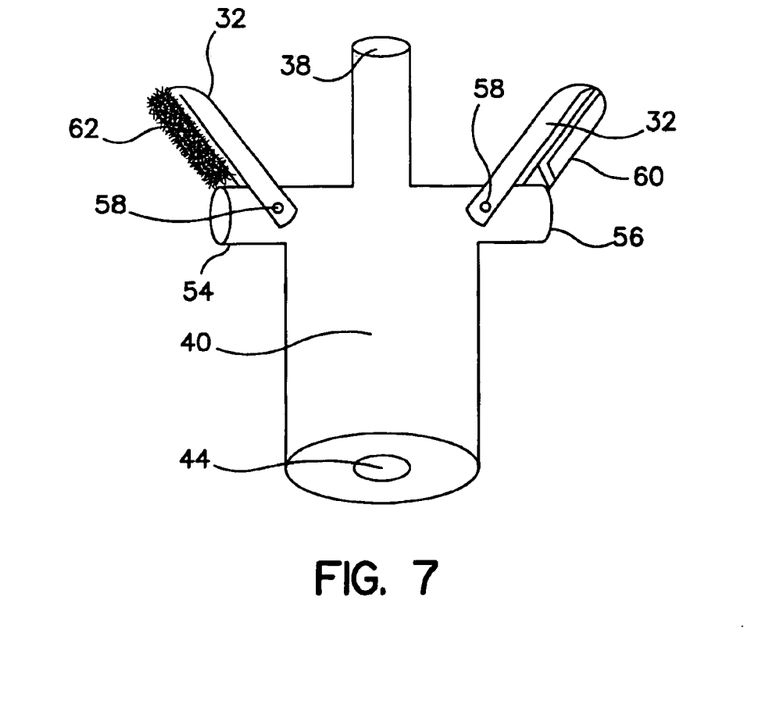
FIG. 7 is a perspective view of a subassembly of the present invention using the component of FIG. 6.

Turning now to FIG. 7, there is shown a perspective view of the T-shaped end tube 40 and showing the articulating members 32 pivotally affixed to the legs 54, 56 of the T-shaped end tube 40. Any means of pivotally affixing the articulating members 32 to the legs 54, 56 can be used that allow the articulating members 32 to pivot as needed in the movement from the retracted position of FIG. 2 to the extended position of FIG. 3 where the articulating members 32 are eventually at about a 90 degree angle to the longitudinal axis of the outer tube 12 (FIG. 3). An example of one of such devices can be a pair of pins 58 that pass through a bifurcated base of the articulating members 32 and also through the arms 54, 56 of the T-shaped end tube 40.

Each of the articulating members 32 has an operative surface that is used to obtain the biopsy sample of tissue from the parietal pleura of a patient. As shown, one of such operative surfaces can be a knife edge 60 that is used to cut the surface of the parietal pleura of a patient to obtain the biopsy tissue while another operative surface may be a brush edge 62 that brushes against the parietal pleura and can pick up cells that are present on the surface. The brush edge 62 may typically be somewhat softer than the bristles of a standard toothbrush and may be preferable made of a bio-compatible plastic material.

Figure 8:
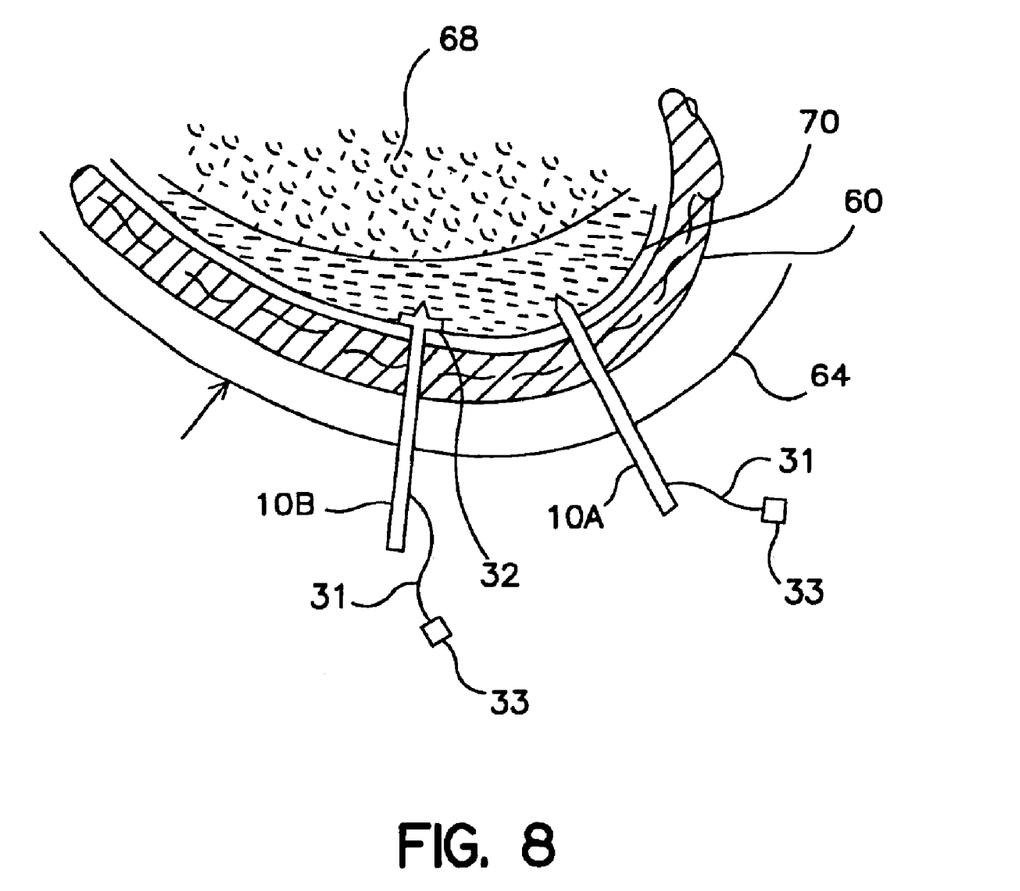
FIG. 8 is a schematic view of a portion of the anatomy of a patient showing the present invention with its articulating members in the extended and retracted positions.

Turning finally to FIG. 8, taken in conjunction with FIGS. 1–7, there is shown a schematic view of the anatomy of a patient and which can be used to illustrate the method of using the biopsy needle 10 of the present invention. In FIG. 8, there can be seen the skin 64, ribcage 66 and further inwardly of a patient is shown a lung 68 of a patient. Intermediate the lung 68 and the ribcage 66 is located the parietal pleura 70 and which is within the plural cavity of a patient. With the present invention, it is desired that the sample of the tissue be obtained from the parietal pleura in order to carry out the further analytical tests on that sample of tissue.

As such, the biopsy needle is show in two stages, that is, there is a biopsy needle 10A constructed in accordance with the present invention with the articulating members 32 in the retracted position and a further biopsy needle 10B that is shown with the articulating members 32 in the extended position and the two different positions of the articulating members 32 will be referred to in describing the method of obtaining the biopsy sample from the parietal pleura 70.

Accordingly, to carry out the method of the present invention, the biopsy needle 10 is inserted through the rib cage 64 such that the distal end 14 of the outer tube 12 is located within the pleural cavity. During this process the articulating members 32 are in the retracted position such that the outer profile of the outer tube 12 is unaffected by the presence of the articulating members 32. As previously explained, the articulating members 32 may be safely contained within the interior of the outer tube 12 or, alternatively, they may be situated within the wall of the outer tube alongside that wall or ever flattened along the exterior of the outer tube 12, it being of importance that the presence of the articulating members 32 do not impede or in any way interfere with the piercing of the patient's skin 66 of the ribcage 64 so that the exterior profile of the outer tube 12 is clean.

Thus, as the biopsy needle 10 reaches the position illustrated as the biopsy needle 10A, the articulating members 32 are moved to their extended positions as depicted by the biopsy needle 10B. It is an assurance to the user that the distal end of the biopsy needle 10 must be properly located in the pleural cavity since otherwise the articulating members 32 would not be readily moved to that extended position. As such, and as opposed to the prior art biopsy needles, the user can be confident that the distal end of the biopsy needle 10 is properly located and that the correct biopsy sample will be obtained from the desired location of the patient. Again, as stated, the moving of the articulating members 32 to the extended position, or, for that matter, back to the retracted position, can readily be accomplished by simply pushing inwardly on the inner tube 24 by means of the user engaging and manipulating the handle 28 that extends outwardly from the outer tube 12, however, the movement of the articulating members 32 may be accomplish by other means and mechanisms, such as by having a threaded connection of the inner tube 24 to the outer tube 12 such that the inner tube can be rotated to move the articulating members 32. Other similar mechanisms may also be employed to move the articulating members 32 between the retracted and extended positions.

Again, the significance is that the user can access the inner tube 24 or some other operating mechanism external of the patient and which can be manipulated by the user to move the articulating members 32 from their retracted position to their extended position. As an example, in the preferred embodiment, there are two articulating members 23, however there may be only one of such articulating members 32 or other number thereof that is practical for use with the present biopsy needle.

In any event, once the articulating members 32 have been manipulated to their extended position illustrated by the biopsy needle 10B, the biopsy needle 10 can be gently moved outwardly with respect to the pleural cavity of the patient so that the articulating members 32 contact the parietal pleura, at which point the entire biopsy needle 10 can be rotated by the user. Such rotation causes the articulating members 32 to move over the parietal pleura and the operative edges of the articulating members 32 can pick up the desired biopsy sample. If the operative edge of an articulating member 32 is the knife edge 60, the biopsy sample will be cut from the parietal pleura and, on the other hand, if the operative edge of the articulating member 32 or members 32 is the brush edge 62, the brush edge 62 will pick up cells and tissue from the parietal pleura. As indicated, if only one articulating member is utilized, the operative edge may be a knife edge or a brush edge, and if two articulating members are utilized, both operative edges may be brush edges, knife edge or may be one of each.

As the biopsy sample is thereupon picked up by the articulating members 32, the articulating members 32 are again returned to their retracted position so that the exterior profile of the outer tube 12 is again a clean profile and the biopsy needle 10 can readily be withdrawn from the patient with the biopsy sample safely contained within the outer tube 12 where that sample can be easily retrieved for analysis.

As can also be seen in FIG. 8, there may be with a fluid withdrawal feature of the present biopsy needle 10 by means of the flexible tube 31 in carrying out the procedure of thoracentesis, and that fluid can be withdrawn by means of any normal withdrawing device that can be readily attached to the connector 33, which, preferably can be a stopcock. A syringe or other withdrawal device is attachable to the connector 33 to create a partial vacuum within the interior area of the outer tube 12 as previously explained, to withdraw the fluids. Thus, along with the use of the present biopsy needle 10 to obtain a sample for the patient, the user can also use the present biopsy needle 10 to remove fluids easily from the patient.

Therefore with the use of the present method and of the present apparatus, a biopsy sample can be obtained from the partial pleura of patient and the user can be assured that only the desired biopsy sample is obtain from the correct location and without danger of puncturing the lung of a patient. In addition, the procedure of thoracentesis is readily carried out with the same biopsy needle.

Those skilled in the art will readily recognize numerous adaptations and modifications which can be made to the present biopsy needle and method of use thereof which will result in an improved device and method yet all of which will fall within the scope and spirit of the present invention as defined in the following claims. Accordingly, the invention is to be limited only by the following claims and their equivalents.

I claim:

1. A biopsy needle for obtaining a sample of tissue within the pleural cavity of a patient, said biopsy needle comprising
an outer tube having a closed distal end, a proximal end and a central canal therethrough, said distal end having a pair of oppositely disposed peripheral openings formed in said outer tube proximate the distal end thereof,
an inner movable member interfitted within said outer tube, said inner movable member having a distal end adapted to be located at about the distal end of said outer tube and a proximal end accessible to a user at the proximal end of said outer tube, said inner movable member being axially movable within said outer tube,
a pair of articulating members affixed to the distal end of said inner movable member, said articulating members being movable between a retracted position within said outer tube and an extended position where said articulating members extend outwardly through said peripheral openings in said outer tube, said pair of articulating members each having an operative surface facing the proximal end of said biopsy needle when in said extended position, wherein said operative surface of one of said articulating members has a brush edge thereon, whereby manipulation of said biopsy needle causes said operative surfaces to contact the pleural cavity of a patient to obtain tissue samples therefrom.

2. A biopsy needle as defined in claim 1 wherein said articulating members are moved between said retracted position and said extended position by manipulation of said proximal end of said inner movable member.

3. A biopsy needle as defined in claim 2 wherein said proximal end of said inner movable member extends axially outwardly from said proximal end of said outer tube so as to allow the manipulation of said proximal end of said inner movable member.

4. A biopsy needle as defined in claim 3 wherein said proximal end of said inner movable member is formed as an enlarged handle for manipulation by a user.

5. A biopsy needle as defined in claim 1 wherein said closed distal end of said outer tube is pointed.

6. A biopsy needle as defined in claim 1 wherein said outer tube has a longitudinal axis and at least one articulating member moves outwardly to a position approximately 90 degrees to the longitudinal axis of said outer tube.

7. A biopsy needle as defined in claim 1 wherein the operative surface of the other of said articulating members has a cutting edge formed thereon.

8. A biopsy needle for obtaining a sample of tissue within the pleural cavity of a patient, said biopsy needle comprising an outer tube having a closed distal end, a proximal end and a central canal therethrough, said distal end having a pair of oppositely disposed peripheral openings formed in said outer tube proximate the distal end thereof, an inner movable member interfitted within said outer tube, said inner movable member having a distal end adapted to be located at about the distal end of said outer tube and a proximal end accessible to a user at the proximal end of said outer tube, said inner movable member being axially movable within said outer tube, wherein said closed distal end of said outer tube has an internal elongated opening, and said inner movable member has a needle shaped end that movably fits within said internal elongated opening to stabilize the axial movement of said inner movable member with respect to said outer tube, a pair of articulating members affixed to the distal end of said inner movable member, said articulating members being movable between a retracted position within said outer tube and an extended position where said articulating members extend outwardly through said peripheral openings in said outer tube, said pair of articulating members each having an operative surface facing the proximal end of said biopsy needle when in said extended position whereby manipulation of said biopsy needle causes said operative surfaces to contact the pleural cavity of a patient to obtain tissue samples therefrom.

9. A biopsy needle for obtaining a sample of tissue within the pleural cavity of a patient, said biopsy needle comprising an outer tube having a closed distal end, a proximal end and a central canal therethrough, said distal end having a pair of peripheral openings formed in said outer tube proximate the closed distal end thereof, an inner movable member interfitted within said outer tube, said inner movable member having a distal end adapted to be located at about the distal end of said outer tube and a proximal end accessible to a user at the proximal end of said outer tube, said inner movable member being axially movable within said outer tube, an end tube affixed to the distal end of said inner movable member, said end tube being T-shaped having a pair of upper legs, said end tube having two articulating members movably affixed thereto and extending from said upper legs of said T-shaped end tube, said articulating members being movable between a retracted position within said outer tube and an extended position where said articulating members extend outwardly through said peripheral openings in said outer tube, said articulating members each having an operative surface facing the proximal end of said biopsy needle when in said extended position whereby manipulation of said biopsy needle causes said operative surfaces to contact the pleural cavity of a patient to obtain tissue samples therefrom.

10. A biopsy needle as defined in claim 9 wherein said proximal end of said outer tube is sealed by an outer tube cover and wherein said proximal end of said inner movable member passes through the outer tube cover.

11. A biopsy needle as defined in claim 10 wherein said outer tube cover is threadedly affixed to the proximal end of said outer tube.

12. A biopsy needle as defined in claim 10 wherein said outer tube cover has outwardly extending wings extending outwardly therefrom.

13. A biopsy needle as defined in claim 9 wherein said proximal end of said inner movable member is enlarged to form a handle to allow manipulation of said inner movable member by a user.

14. A biopsy needle as defined in claim 9 wherein said inner movable member includes a stop means to limit the axial movement of said inner movable member outwardly from said outer tube.

15. A biopsy needle as defined in claim 14 wherein said stop means comprises a enlarged diameter member affixed to said inner movable member that engages said outer tube cover when said inner movable member is moved outwardly with respect to said outer tube.

16. A biopsy needle as defined in claim 9 wherein said outer tube has a flexible tube affixed at about the proximal end thereof, said flexible tube communicating with the interior area of said outer tube and having a connector affixed to a free end of said flexible tube to remove fluids from a patient.

17. A biopsy needle for obtaining a sample of tissue within the pleural cavity of a patient, said biopsy needle comprising an outer tube having a closed distal end, a proximal end and a central canal therethrough, said distal end having a pair of peripheral openings formed in said outer tube proximate the closed distal end thereof, an inner movable member interfitted within said outer tube, said inner movable member having a distal end adapted to be located at about the distal end of said outer tube and a proximal end accessible to a user at the proximal end of said outer tube, said inner movable member being axially movable within said outer tube, an end tube affixed to the distal end of said inner movable member, wherein said end tube has an axial needle shaped end extending therefrom and said distal end of said outer tube has an elongated recess formed therein, said axially extending needle shaped end of said end tube adapted to slidingly interfit within said elongated recess to guide the axial movement of said inner movable member, said end tube having two articulating members movably affixed thereto and extending from said end tube, said articulating members being movable between a retracted position within said outer tube and an extended position where said articulating members extend outwardly through said peripheral openings in said outer tube, said articulating members each having an operative surface facing the proximal end of said biopsy needle when in said extended position whereby manipulation of said biopsy needle causes said operative surfaces to contact the pleural cavity of a patient to obtain tissue samples therefrom.

18. A biopsy needle for obtaining a sample of tissue within the pleural cavity of a patient, said biopsy needle comprising an outer tube having a closed distal end, a proximal end and a central canal therethrough, said distal end having a pair of peripheral openings formed in said outer tube proximate the closed distal end thereof, an inner movable member interfitted within said outer tube, said inner movable member having a distal end adapted to be located at about the distal end of said outer tube and a proximal end accessible to a user at the proximal end of said outer tube, said inner movable member being axially movable within said outer tube, an end tube affixed to the distal end of said inner movable member, said end tube having two articulating members movably affixed thereto and extending from said end tube, said articulating members being movable between a retracted position within said outer tube and an extended position where said articulating members extend outwardly through said peripheral openings in said outer tube, said articulating members each having an operative surface facing the proximal end of said biopsy needle when in said extended position, wherein at least one of said articulating members has an operative surface having a brush edge thereon whereby manipulation of said biopsy needle causes said operative surfaces to contact the pleural cavity of a patient to obtain tissue samples therefrom.

19. A biopsy needle as defined in claim 18 wherein the operative surface of the other of said articulating members has a cutting edge formed thereon.

20. A method of obtaining a sample of tissue from the pleural cavity of a patient, said method comprising the steps of:

providing a needle having a closed distal end with at least one articulating member having a brush edge formed thereon movable between a retracted position and an extended position extending outwardly from the needle proximate to the closed distal end of the needle, inserting the needle into a patient such that the distal end of the needle is located within the pleural cavity of the patient, extending the at least one articulating member outwardly from the needle, adjusting the location of the needle to cause the at least one articulating member to contact the parietal pleura of the patient, rotating the needle to move the at least one articulating member to pick up a sample of the pleura onto the at least one articulating member, retracting the at least one articulating member to the retracted position, and removing the needle from the patient to collect a sample of the pleura adhered to the at least one articulating member.

21. A method of obtaining a sample of tissue from the pleural cavity of a patient as defined in claim 20 said step of providing a needle comprises providing a needle having a retracted position wherein said at least one articulating members is fully contained within the needle.

22. A method of obtaining a sample of tissue from the pleural cavity of a patient as defined in claim 20 wherein said step of providing a needle comprises providing a needle having two articulating members.

23. A method of obtaining a sample of tissue from the pleural cavity of a patient as defined in claim 20 wherein said step of providing a needle comprises providing a needle having two articulating members with one articulating member having a knife edge formed thereon and the other articulating member having a brush edge formed thereon.

* * * * *